(12) United States Patent
Lysgaard (10) Patent No.: US 10,813,786 B2
(45) Date of Patent: Oct. 27, 2020

(54) DRAINABLE COLLECTION BAG

(71) Applicant: Coloplast A/S, Humlebaek (DK)

(72) Inventor: Jes Lysgaard, Havdrup (DK)

(73) Assignee: Coloplast A/S, Humlebaek (DK)

( * ) Notice: Subject to any disclaimer, the term of this patent is extended or adjusted under 35 U.S.C. 154(b) by 426 days.

(21) Appl. No.: 15/326,496

(22) PCT Filed: Jul. 10, 2015

(86) PCT No.: PCT/DK2015/050213
§ 371 (c)(1),
(2) Date: Jan. 16, 2017

(87) PCT Pub. No.: WO2016/008495
PCT Pub. Date: Jan. 21, 2016

(65) Prior Publication Data
US 2017/0209297 A1    Jul. 27, 2017

(30) Foreign Application Priority Data

Jul. 16, 2014  (DK) .................................. 2014 00390

(51) Int. Cl.
*A61F 5/44* (2006.01)
*A61F 5/445* (2006.01)

(52) U.S. Cl.
CPC .......... *A61F 5/4407* (2013.01); *A61F 5/4404* (2013.01); *A61F 5/445* (2013.01)

(58) Field of Classification Search
CPC combination set(s) only.
See application file for complete search history.

(56) References Cited

U.S. PATENT DOCUMENTS

| | | | | | |
|---|---|---|---|---|---|
| 4,233,977 | A | * | 11/1980 | Mattson | A61F 5/4407 604/335 |
| 4,403,991 | A | * | 9/1983 | Hill | A61F 5/443 604/337 |
| 4,465,486 | A | * | 8/1984 | Hill | A61F 5/443 24/30.5 R |
| 4,755,177 | A | * | 7/1988 | Hill | A61F 5/443 604/336 |
| 4,988,343 | A | * | 1/1991 | Ballan | A61F 5/4407 383/66 |
| 5,968,023 | A | * | 10/1999 | Olsen | A61F 5/4407 604/334 |
| 6,336,918 | B1 | * | 1/2002 | Olsen | A61F 5/4407 604/332 |

(Continued)

FOREIGN PATENT DOCUMENTS

CN    1193720 A    9/1998
CN    1379646 A    11/2002
(Continued)

*Primary Examiner* — Nicholas J. Weiss
*Assistant Examiner* — Guy K Townsend
(74) *Attorney, Agent, or Firm* — Coloplast Corp., Coloplast A/S; Nick Baumann (57) ABSTRACT

A drainable collecting bag for human body wastes may comprise a front wall and a rear wall of flexible sheet material defining a cavity there between and which may define a downwardly extending neck portion terminating in a discharge opening. The discharge opening can be folded upwards into a closed configuration for liquid tight closure of the bag and the folded closure may be fixed by angled fastening strips.

13 Claims, 9 Drawing Sheets

(56) References Cited

U.S. PATENT DOCUMENTS

| | | | | |
|---|---|---|---|---|
| 6,419,664 B1* | 7/2002 | von Bulow | A61F 5/4407 | 604/317 |
| 6,589,221 B1* | 7/2003 | Olsen | A61F 5/4407 | 604/332 |
| 2003/0028160 A1* | 2/2003 | Leise, Jr. | A61F 5/4407 | 604/334 |
| 2003/0073962 A1* | 4/2003 | Olsen | A61F 5/445 | 604/327 |
| 2003/0153882 A1* | 8/2003 | Mandzij | A61F 5/4407 | 604/334 |
| 2003/0167042 A1* | 9/2003 | Poulsen | A61F 5/4407 | 604/327 |
| 2004/0049837 A1* | 3/2004 | Falconer | A61F 5/4407 | 4/144.1 |
| 2004/0068243 A1* | 4/2004 | Hansen | A61F 5/4407 | 604/327 |
| 2005/0159717 A1* | 7/2005 | Holtermann | A61F 5/4407 | 604/332 |
| 2007/0265588 A1* | 11/2007 | Pedersen | A61F 5/4407 | 604/337 |
| 2008/0033379 A1* | 2/2008 | Pedersen | A61F 5/4407 | 604/335 |
| 2008/0097360 A1* | 4/2008 | Andersen | A61F 5/44 | 604/332 |
| 2009/0082743 A1* | 3/2009 | Buglino | A61F 5/445 | 604/335 |
| 2009/0143755 A1* | 6/2009 | Schertiger | A61F 5/445 | 604/345 |
| 2010/0217214 A1* | 8/2010 | Hansen | A61F 5/4407 | 604/327 |
| 2011/0028923 A1* | 2/2011 | Murray | A61F 5/4405 | 604/332 |
| 2011/0028924 A1* | 2/2011 | Murray | A61F 5/4407 | 604/332 |
| 2012/0022477 A1* | 1/2012 | Grum-Schwensen | A61F 5/443 | 604/332 |
| 2012/0022478 A1* | 1/2012 | Friske | A61F 5/4407 | 604/335 |
| 2013/0253456 A1* | 9/2013 | Friske | A61F 5/445 | 604/332 |
| 2014/0163495 A1* | 6/2014 | Nassopoulos | A61F 5/443 | 604/338 |
| 2017/0209297 A1* | 7/2017 | Lysgaard | A61F 5/445 | |

FOREIGN PATENT DOCUMENTS

| | | |
|---|---|---|
| RU | 2220685 C1 | 1/2004 |
| RU | 128102 U1 | 5/2013 |
| WO | 9966859 A2 | 12/1999 |
| WO | 2007115575 A1 | 10/2007 |
| WO | 2008141652 A1 | 11/2008 |
| WO | 2009124324 A1 | 10/2009 |

* cited by examiner

DRAINABLE COLLECTION BAG

FIELD OF THE INVENTION

The invention relates to a drainable collecting bag having improved closure.

BACKGROUND OF THE INVENTION

Drainable collecting bags is often used as ostomy bags. In the case of ileostomy patients and colostomy patients with uncontrolled release of faeces of a more or less fluid consistence, the collecting bag has to be emptied rather frequently, and the closure device thus has to be easy to open and re-close after emptying and at the same time provide a reliable and tight seal in operation, i.e. between emptying the bag.

Such a bag typically has flat opposing sidewalls secured together along their edges and defining a cavity for receiving body waste material. One of the walls is provided with a stoma-receiving opening, and means are provided for securing the bag to a patient's abdomen so that waste discharge from the stoma is received in the cavity. At is lower end, the drainable bag has a discharge opening for draining waste material, usually provided at the end of a narrowed neck portion. Closure means is provided for maintaining the discharge opening in sealed condition until such time as waste material is to be drained from the bag. The closure means may take the form of a clamp or some device for securing the neck portion in upwardly-rolled condition. As will be appreciated, conventional wire ties or wraps have also been used for that purpose.

A drainable bag is reusable following periodic emptying of waste material, but cleaning is necessary prior to reuse so that effective sealing can be assured and odors emanating from the resealed bag can be avoided. Users often encounter difficulty and discomfort in unsealing, emptying, cleaning and resealing drainable bags because of the direct exposure to waste material and because the manipulations may require greater dexterity than a patient, particularly an elderly patient, can provide. Adding to the problem is the fact that residual amounts of solid and/or liquid waste matter at the lower end of a drainage bag tends to block or hold the walls of the bag together, making cleaning of the inside surfaces adjacent the discharge opening even more difficult.

BRIEF DESCRIPTION OF DRAWINGS

FIG. 1a is a front elevational view of a drainable collection bag having a first and a second plate bordering the discharge opening and angled fastening strips.

FIG. 1b is a cross section of the lower part of the drainable collection bag of FIG. 1a.

FIG. 2 is a rear elevational view of the drainable collection bag of FIG. 1a.

SUMMARY OF THE INVENTION

A drainable collecting bag for human body wastes may comprise a front wall and a rear wall of flexible sheet material defining a cavity there between and which may define a downwardly extending neck portion terminating in a discharge opening. The discharge opening can be folded upwards into a closed configuration for liquid tight closure of the bag and the folded closure may be fixed by angled fastening strips.

DETAILED DESCRIPTION OF THE INVENTION

In a first aspect, the invention relates to a drainable collecting bag for human body wastes, comprising a front wall and a rear wall of flexible sheet material defining a cavity there between and which define a downwardly extending neck portion terminating in a discharge opening, a first and a second plate member, the first and the second plate members comprising at least a first edge portion and a second edge portion, the first plate member being attached to the front wall and the second plate member attached to the rear wall, the bag is configured to be closed by folding the neck portion upwardly, the bag further comprises fastening strips for securing the folded neck portion in closed position, wherein the fastening strips extend from the neck portion and define an angle of angle of 75-15 degrees with the discharge opening.

The first edge of the first plate member and the first edge of the second plate member may be facing each other and said discharge opening is extending between said edges.

In embodiments, the first and the second plates are non-adhesive. By non-adhesive should herein be understood that the surface of the plates does not show adhesive properties. This facilitates easy cleaning of the plates.

One or both plates may be configured to be able to pivot 180 degrees around the first edge portion with respect to the front and the rear wall. By the first and the second plates being configured to be able to pivot 180 degrees around the first edge portion with respect to the front and the rear wall is meant that the first and the second plate are attached to the front and the rear wall at least along the first edge portion and that they are able to pivot freely around an axis corresponding to the first edge portion. Thus, the plates are able to pivot around the first edge portion without folding the neck portion.

One of the plates may be attached to the walls in such a way they cannot pivot with respect to the front and rear wall.

The neck portion is configured to be folded into a closed configuration by folding the neck portion around the plates and an open configuration where the neck portion is unfolded facilitating emptying the contents from the cavity.

The plates being able to pivot with respect to the neck portion enables them to be configured in a discharge configuration where the plates are lying towards the sidewalls such that a first surface of the plates are facing the surface of the neck portion (front and rear wall). Thus, the first surfaces of the plates are facing each other's, with the neck portion in between. In this configuration the user may squeeze the content out of the bag using his fingers applying pressure to the neck portion and his fingers will be protected from contamination with the content of the bag by the plates. If the plates are not attached along the side edge of the neck portion, they can be slightly lifted in order to assure the entire content is squeezed out of the neck portion next to the discharge opening. If the plates are extending further than the width of the neck portion, the extended portion (tab member) may serve as a handle. When the bag is emptied, the discharge opening can easily be cleaned by wiping as only the first edges of the plates will be smudged. Cleaning will be easier as the only part of the bag that becomes dirty is the edges of the opening/plates, and this can be easily wiped clean.

When the bag is emptied and the closure is cleaned, the plates may be inverted to the opposite configuration, by pivoting one or both the plates 180 degrees with respect to the neck portion. Now the second surface of the first plate is facing the second surface of the second plate. In this configuration the plates may be placed overlying each other's and in direct contact, without the neck portion in between. Now the plates are pressed firmly together and the combined plates are folded towards the neck portion to lye against the walls of the neck portion. The flexible material of the plates squeezes together and at the same time the sidewalls of the neck portion stretches and the outlet is sealed. Folding is continued so the neck portion are wrapped around the combined plates to provide a tight and effective closing of the bag.

The front and/or rear walls of the bag may be provided with a cover layer which is soft and pleasant to have against the skin. The cover layer may be attached along the edge portion of the bag for example by welding or adhesive. The cover layer may preferably not extend to the neck portion. The cover layer may be provided with a slit or in a two-part system allowing the user to inspect the content of the cavity. The cover layer may be in the form of a non-woven material. The cover layer may be opaque or non-transparent in order to hide the content of the bag.

The neck portion may be rolled or folded at least one, such as two times around the plates to create a waterproof closure of the bag.

In order to avoid unintended unfolding of the neck portion, the bag may be provided with locking means.

The locking means may be in the form of hook-and-loop system such as Velcro or it may be an adhesive, pressure studs or other suitable locking means. The locking means may be in the form of one or more parts being provided at least on the fastening strips. A counterpart of the locking means may be provided at the neck portion. One part (such as the loops) may be provided on the fastening strips and the other part (such as the hooks) on the neck portion.

The locking means may be provided on fastening strips. The strips may be elongated strips extending from the side edges of the front and rear wall. The strips may be made from the same material as the front and rear wall and may constitute a part of the rear and front wall. The strips may be reinforced in order to provide extra strength or stiffness.

The fastening strips may be located in a non-parallel manner with regard to the discharge opening. The direction of the discharge opening corresponds to the line of the first edges of the plates. The angle of the fastening strips with regard to the discharge opening is defined as the angle to a line drawn along the first edges of the plates, this line being substantially perpendicular to the vertical axis of the bag and neck portion.

The fastening strips is mounted in an angle of 75-15 degrees, such as 60-30 degrees, such as 55-35 degrees or even such as 50-40 degrees with the discharge opening. The fastening strips may define an angle of approximately 45 degrees with respect to the discharge opening.

The angled fastening strips provide better fixation of the folded/rolled neck portion by crossing the folding. The angled fastening strips may be pointing towards the cavity in the sense that the fastening strips are pointing/away from the discharge closure or the fastening strips may point away from the cavity.

The collection bag may comprise a two-part fastening system for selectively and releasably holding the neck portion in upwardly folded condition; the system including a first fastener part located along the outer surface of one of the sidewalls of the neck portion and a second fastener part located on the fastening strips; the first and second fastener parts configured to be wrapped around the upwardly folded neck portion and to be brought into mutual engagement and attachment when the neck portion is in its fully folded condition.

The plates may be in the form of a sheet like material comprising at least a first and a second edge portion and a first and a second surface. The plates may be mirror images of each other's. The plates comprise a flexible material such as a polymer sheet or a closed cell foam sheet.

The first edge portion of the plate members may have a length at least corresponding to the width of the discharge opening or it may have a length extending further than the width of the discharge opening.

The second edge portion may have the same length as the first edge portion. The second edge portion may have a length extending further than the width of the discharge opening, thereby providing a part of the plates extending further than the width of the neck portion.

The first and the second edge portion of each plate may be connected by a sloping edge portion. The sloping edge portion may define an angle corresponding to the angle of the fastening strips or a mirror image of this angle. This enables a snug fit of the fastening strips around the folded neck portion and plates when the bag is in closed configuration and a better fixation of the folded neck portion even when it is exposed to pressure from a filled bag.

The sloping edge portion may define an angle of approximately 45 degrees with the discharge opening such as 75-15 degrees, 60-30 degrees, 55-35 degrees or even 50-40 degrees with the discharge opening.

The first and the second plate may be provided with a tab member. The tab member may constitute the part of the plates extending further than the width of the neck portion. The tab member may be designed for easy gripping with the fingers and may ease handling of the bag during emptying. The tabs may enable better hold and control of the opening and the bag during emptying of the bag when the content of the bag is squeezed out.

The first and the second edge portion of the plate members may be substantially parallel.

The first and the second plate members may be connected by at least two strap members. The strap members may be located on each side of the discharge closure. The strap members may be formed integrally with the plate members, said strap members and plate members forming a unit, for example being provided as a single molded unit.

The straps may be provided with indentations or a thinner area at the transition between the plates in order to facilitate easy bending of the strap when the plates are pivoted. The strap may be an integrated part of the plates, being cut or molded together.

The plates may be attached to the side walls of the bag by welding or adhesive or other suitable way. The plate may be attached in a way that enables at least one of the plates to pivot freely around the first edge. The walls may extend further over at least a part of the plate but in a way that allows the plate to pivot with respect to the wall to which it is attached.

The plates provide a handle as well as they offer protection for the user from contaminating his fingers with faeces during emptying of the bag.

A drainable collection bag has typically flat opposing sidewalls secured together along their edges and defining a cavity for receiving body waste material. One of the walls is provided with a stoma-receiving opening, and means are provided for securing the bag to a patient's abdomen so that waste discharge from the stoma is received in the cavity. At is lower end, the drainable bag has a discharge opening for draining waste material, provided at the end of a narrowed neck portion.

The collection may include a two-part fastening system for selectively and releasably holding the neck portion in upwardly folded condition; the system including a first locking means located along the outer surface of one of the sidewalls of the neck portion and a second locking means located on the fastening strips; the first and second locking means being configured to be wrapped around and to be brought into mutual engagement and attachment when the neck portion is in its fully folded condition.

Other advantages and features of the invention will become apparent from the following specification when considered in view of the accompanying drawings.

DETAILED DESCRIPTION OF THE DRAWING

Figures 1A, 1B:
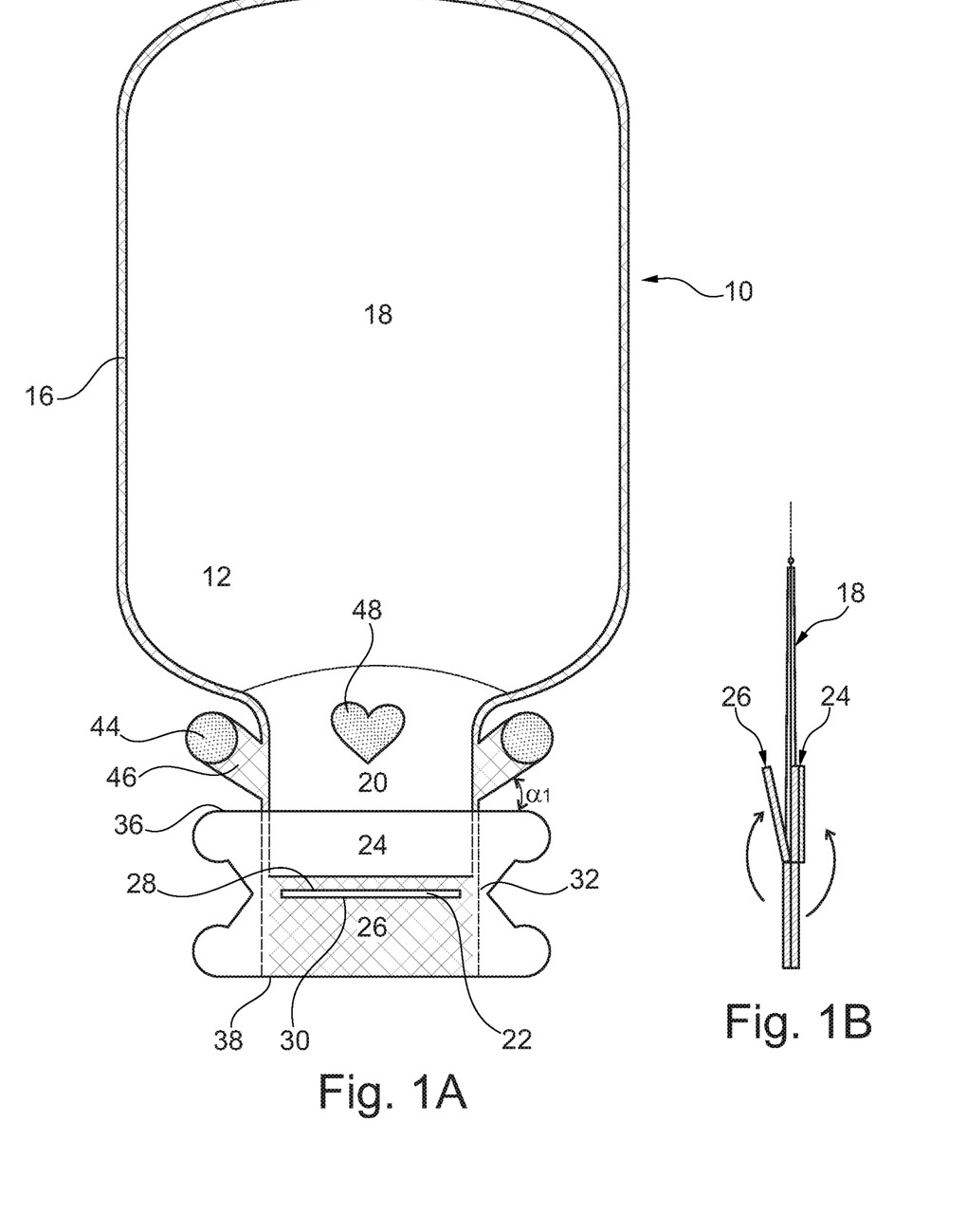
Figure 2:
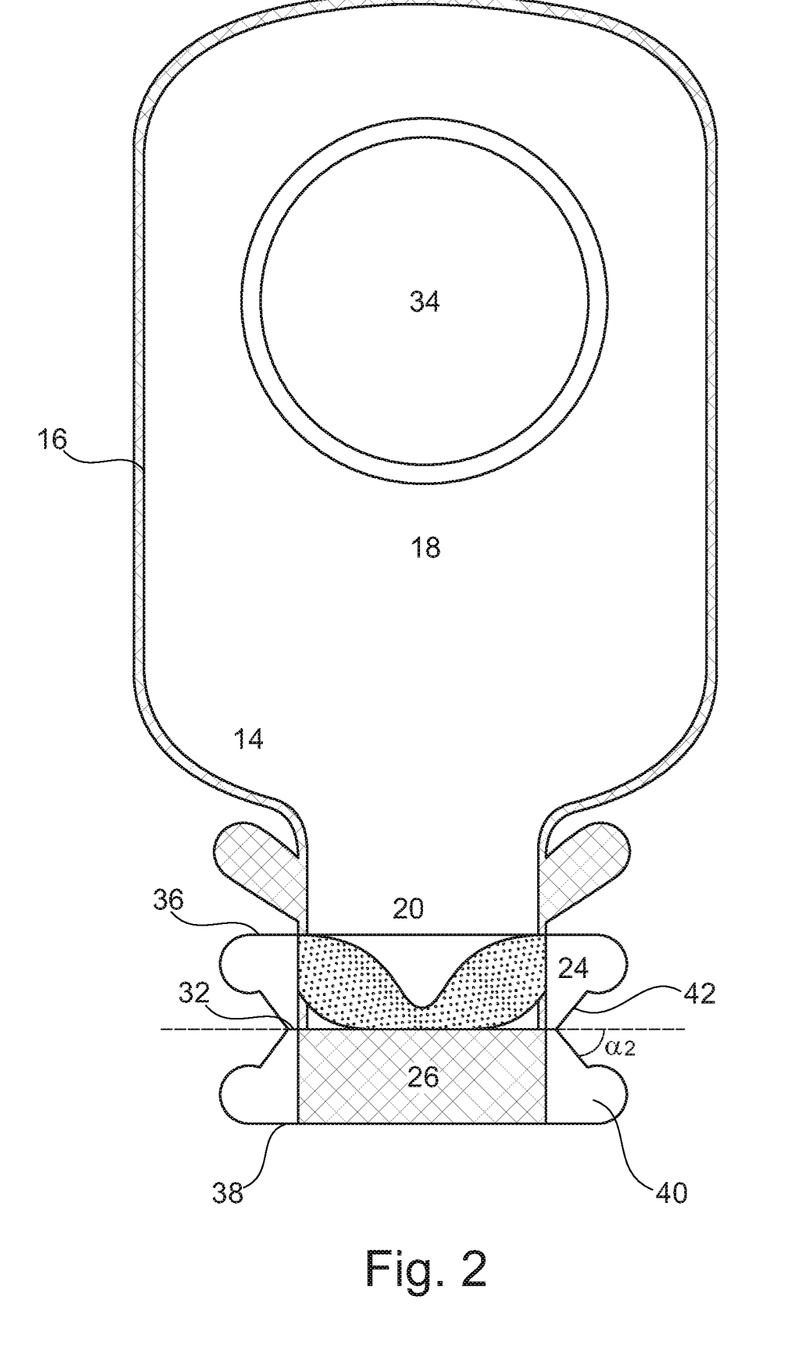

Referring to FIGS. 1A, 1B and 2 of the drawings, the numeral 10 designates a drainable ostomy bag having generally parallel sidewalls of flexible sheet material in the form of a front wall 12 and a rear wall 14. The front wall 12 is facing away from the skin. The sidewalls 12 and 14 are joined along their edges as at 16 to define a cavity 18 there between. They also define a downwardly-extending neck portion 20 which terminates in a discharge opening 22. The bag can be closed by folding the neck portion 20 upwardly and opened by unfolding the neck portion 20 downwardly for draining the contents from the cavity 18.

The discharge opening 22 is bordered with a first and a second plate 24 and 26, each plate 24, 26 comprising at least a first edge portion 28 and a second edge 30 portion. The first and the second plates 24, 26 are connected by a two strap members 32 at the edge of the discharge opening, thereby surrounding the discharge opening 22. The plates 24, 26 are attached to the opening 22 of the bag along the first edge portion 28, 30 enabling the plates to be pivoted, without folding the neck portion, approximately 180 degrees around their attachment line 28, 30 (being the first edge) with respect to the neck portion 20.

With the arrangement illustrated in FIGS. 1A, B and 2, the sidewalls 12, 14 are formed of a flexible plastic film that is substantially water and gas impermeable. One of the sidewalls 14 (the rear or body side wall) is provided with a stoma-receiving waste inlet opening 34 surrounded by means for attaching the drainable ostomy bag 10 to a patient.

The attaching means may take the form of a coupling device provided for detachably securing the drainable bag 10 to an adhesive faceplate/wafer which together define a two-piece appliance. Alternatively, the bag may be a one-piece appliance with an integral and non-separable faceplate/wafer.

The second edge of the plates 36, 38 may be longer than the first edge 28, 30. The second edge 36, 38 may be longer than the width of the discharge opening 22 and extend into a tab member 40. The first 28,30 and the second edges 36,38 are connected with a sloping edge line 42, the line defines an angle α2 with the discharge opening 22/first edge 28,30.

Figure 4:
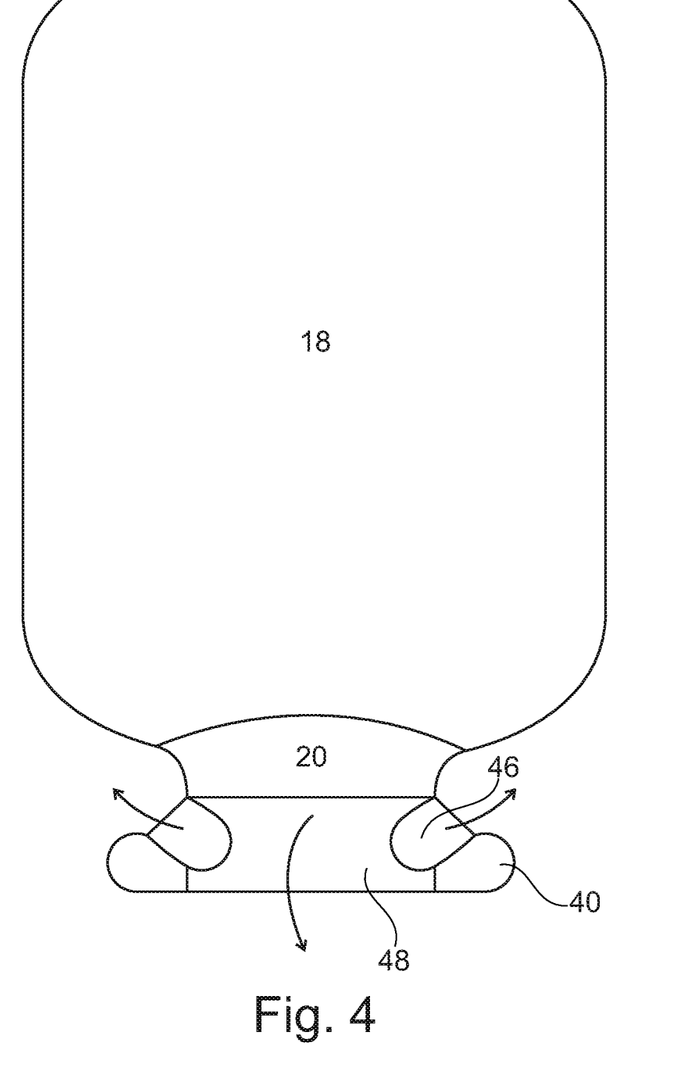
FIG. 4 is a schematic front elevational view of the drainable collection bag with the neck portion folded into closed configuration and fixed with the fastening strips.
Figure 5:
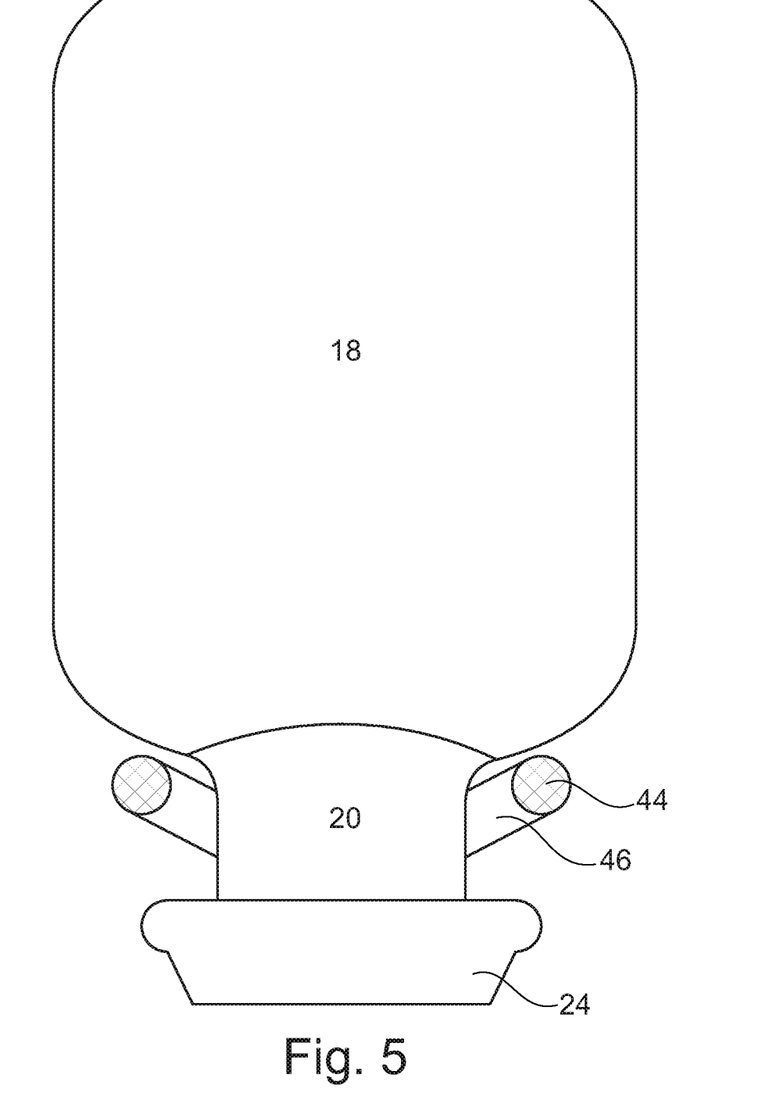
FIG. 5 is a schematic front elevational view of the drainable collection bag with the neck portion unfolded and in open configuration and with the plates closed.
Figure 6:
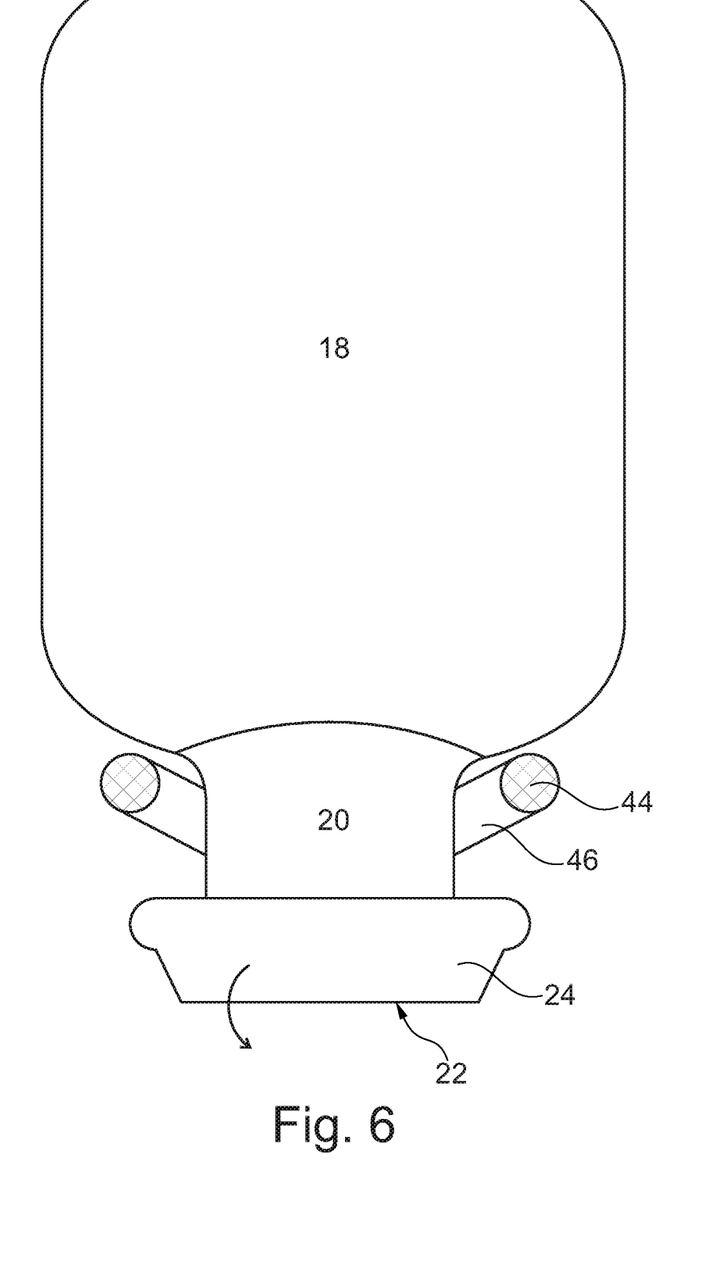
FIGS. 6 and 7 are schematic front elevational views of the drainable collection bag with the neck portion unfolded and in open configuration and with the plates being inverted.
Figure 7:
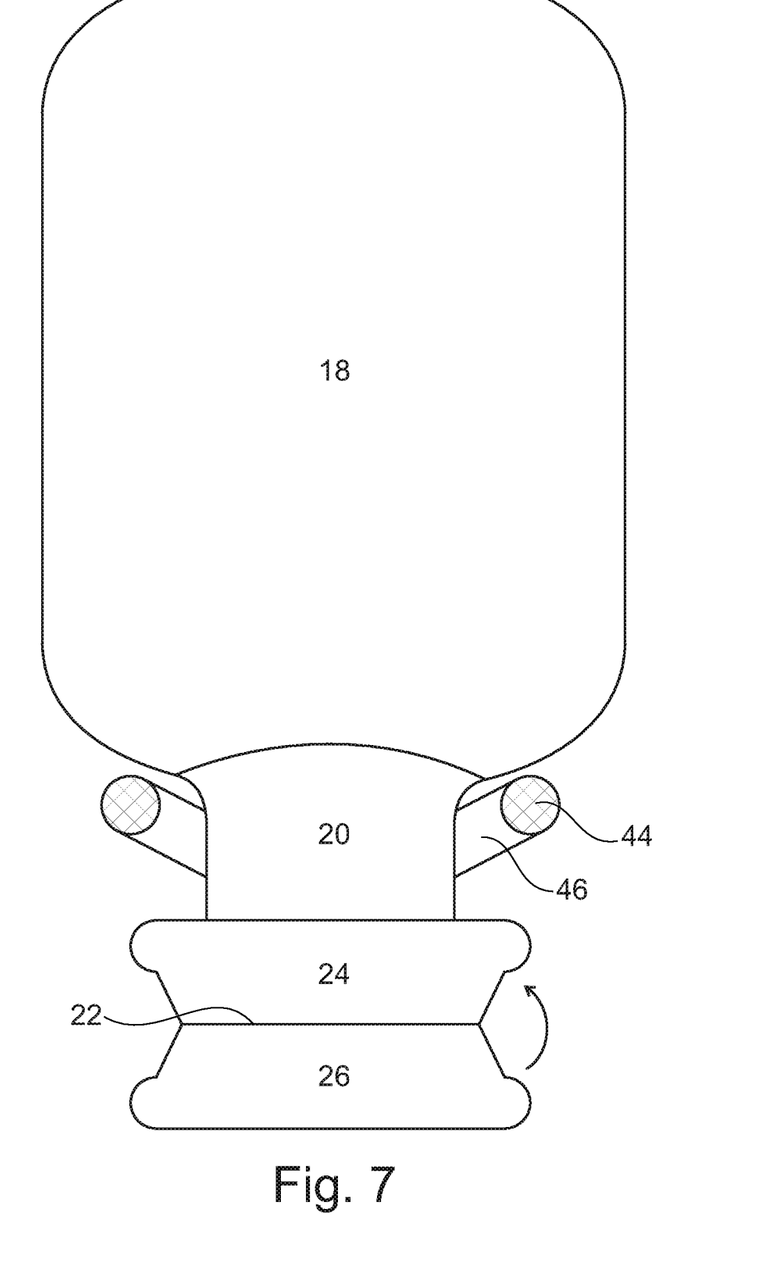

Referring once again to FIGS. 1A and 1B, the drainable ostomy bag will also be seen to include a two-part fastener system for selectively holding the neck portion 20 in upwardly folded condition as best shown in FIG. 4. The two-part fastener system includes locking means in the form of a first part 44 associated with one of the fastening strips 46 extending from the neck portion 20. A second part 48 is provided on the rear wall of the neck portion or on the second first surface of the plate and engages the first part of the locking means when the fastening strip 46 is bended around the folded neck portion. The fastening strips 46 are defining an angle α1 with the discharge opening 22 corresponding substantially to the angle of the sloping edge line of the plates.

Figure 3:
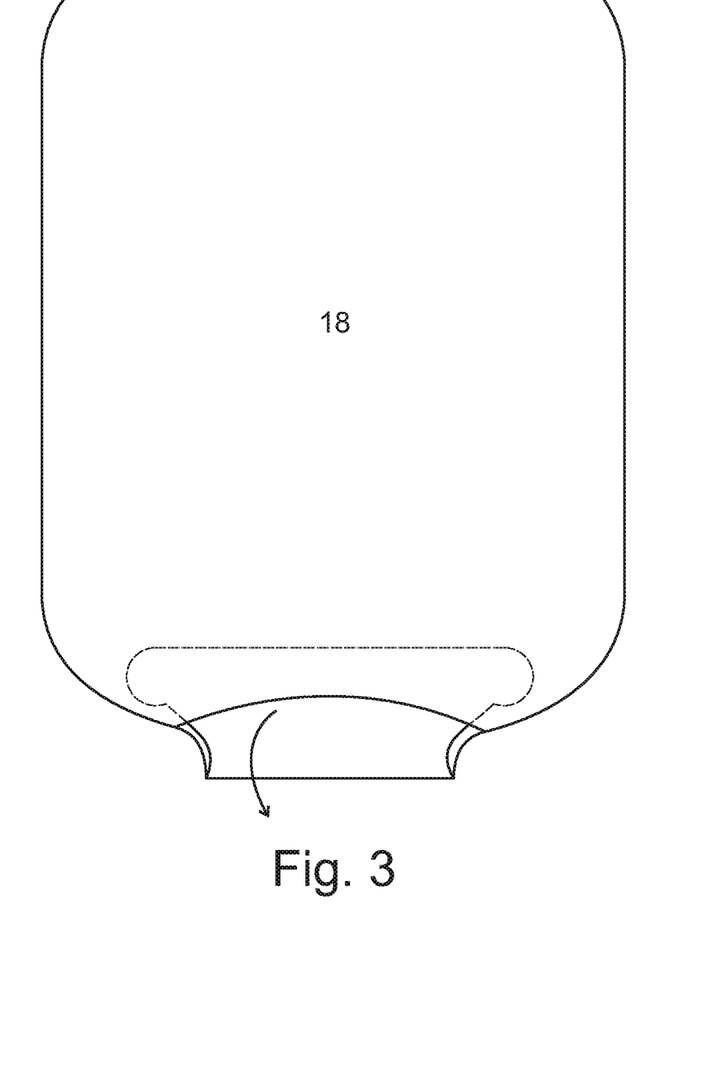
FIG. 3 is a schematic front elevational view of the drainable collection bag with the neck portion folded into closed configuration and partly hidden behind the cover layer.

In FIGS. 3-7 is shown the unfolding of the neck portion 20 from a closed configuration to an open configuration. The neck portion can be folded up into a closed configuration by facing the first surface of the first plate towards the first surface of the second plate, holding the two surfaces firmly together while folding the neck portion around them, thereby providing a liquid tight seal. When the neck portion is folded up, the fastening strips are engaged to be fixed around the folded neck portion/plates and attaching them to the neck portion. The slanting fastening strips provide better fixation of the folded/rolled neck portion by crossing the folding. After the folded neck portion is fixed by the strips it may be folded one more time and hidden behind the cover layer of the bag as shown in FIG. 3.

Figure 8:
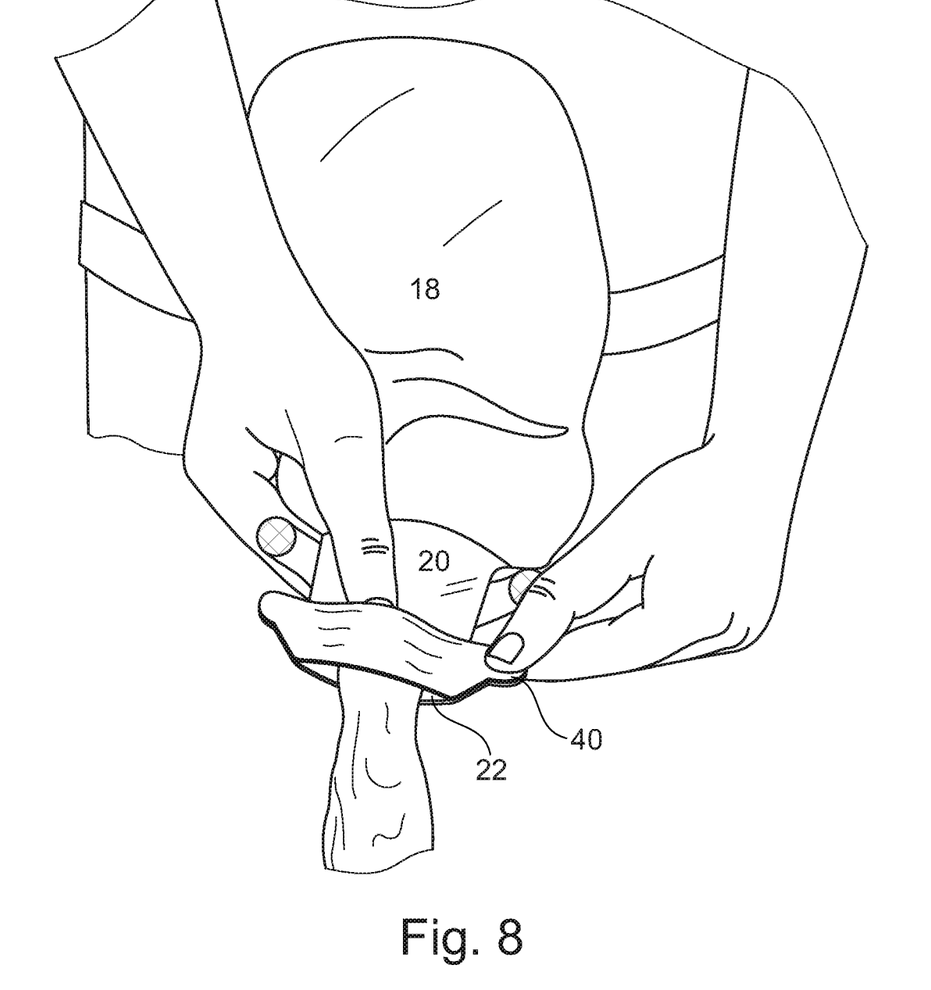
FIG. 8 is a front elevational view of the drainable collection bag where the content of the cavity is discharged.
Figure 9:
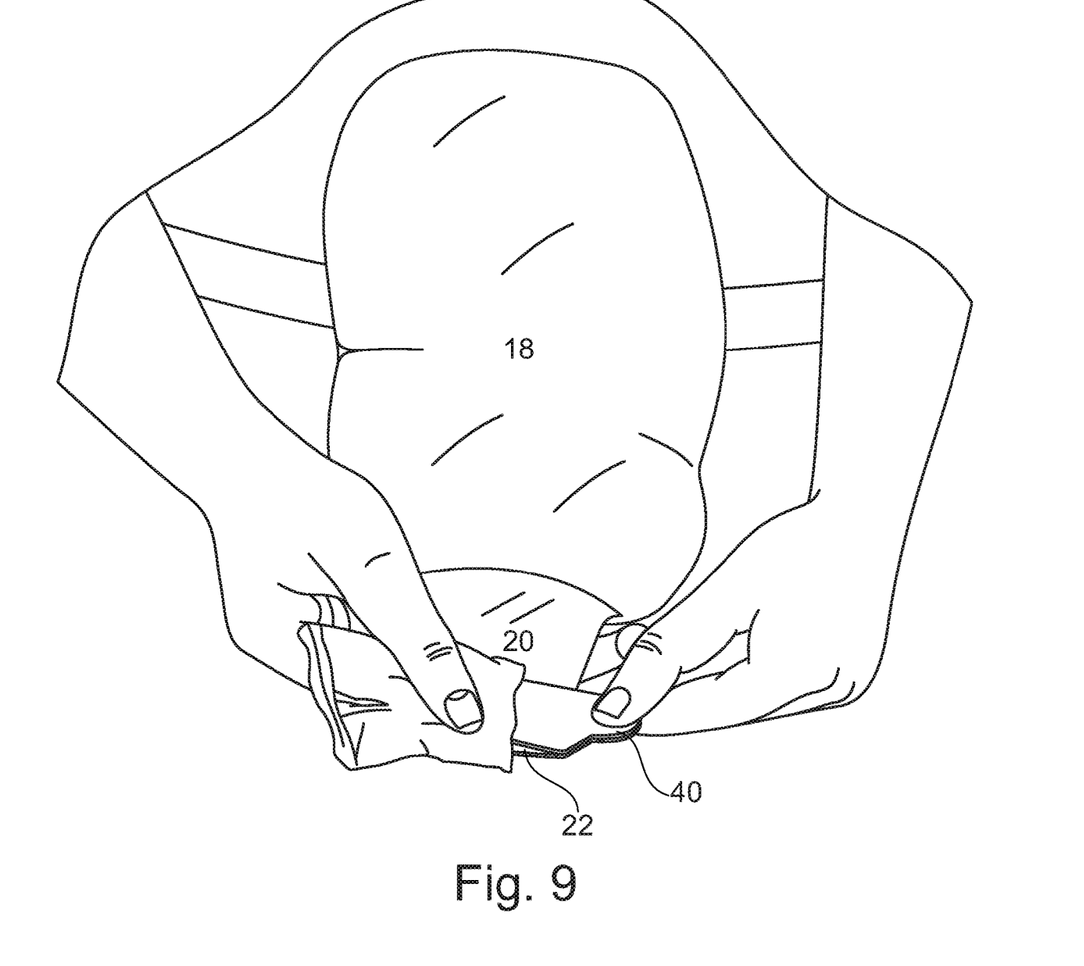
FIG. 9 is a front elevational view of the drainable collection bag where the discharge opening is wiped clean after discharge of content.

When the bag needs to be emptied, the fastening strips 46 are detached, and the neck portion 20 is unfolded/unrolled. The plates are folded back to bring second surfaces together (with the neck portion in between) and the content of the bag is poured/squeezed out of the bag, holding the extended portion 40 of the plates together, see FIG. 8. The last residues of content can be pressed out by putting the fingers between the plate and the neck portion and squeeze. The fingers are protected from contamination by the plate and the construction allows for total emptying of the bag as the entire outer surface of the neck portion can be accessed without getting fingers greased by holding the tab members which extend further than the width of the neck portion. The discharge closure is then wiped clean while holding the tab member, see FIG. 9.

While in the foregoing there have been set forth preferred embodiments of the invention, it will be appreciated that the details herein given may be varied by those skilled in the art without departing from the true scope and spirit of the appended claims.

The invention claimed is:

1. A body waste collecting bag, the bag comprising:
    a front wall joined to a rear wall along a sealed edge of both of the front wall and the rear wall to form a waste collection cavity between the front wall and the rear wall;
    an inlet hole formed in the rear wall and communicating with the waste collection cavity;

a neck portion forming a discharge opening for the waste collection cavity, the discharge opening formed in the bag between a first unsealed edge of the front wall and a second unsealed edge of the rear wall;

a first plate having a first edge and a second edge, the first edge of the first plate aligned with the first unsealed edge of the front;

a second plate having a first edge and a second edge, the first edge of the second plate connected to the second unsealed edge of the rear wall; and a first fastening strip coupled to the neck portion of the bag, with the first fastening strip terminating at a fastener surface located a first distance away from the neck portion;

wherein the first edge of the first plate is longer than a width of the neck portion of the bag and the second edge of the first plate is longer than the first edge of the first plate;

wherein the second edge of the first plate extends between a first tab on a first side of the neck portion and a second tab on a second side of the neck portion to locate the first tab and the second tab laterally away from the neck portion of the bag;

wherein the first tab and the second tab each taper along an edge line to connect with a shorter first edge of the first plate.

2. The bag of claim 1, further comprising a second fastening strip extending away from the neck portion on a side of the neck portion opposite from the first fastening strip.

3. The bag of claim 1, wherein the fastener surface of the first fastening strip comprises a hook and loop fastener.

4. The bag of claim 1, wherein the fastener surface of the first fastening strip comprises an adhesive fastener.

5. The bag of claim 1, further comprising:
a coversheet applied over the front wall, the cover sheet defining a pocket sized to receive the first plate and the second plate.

6. The bag of claim 1, wherein the first tab is offset away from the neck portion by a distance equal to the offset of the second tab away from the neck portion.

7. The bag of claim 6, wherein the first tab is configured to mate with the second tab when the neck portion is folded into a closed configuration.

8. The bag of claim 1, wherein the first edge of the first plate and the first edge of the second plate each has a width equal to a width of the neck portion and the second edge of the first plate and the second edge of the second plate each has a width that is larger than the width of the neck portion.

9. A body waste collecting bag, the bag comprising:
a front wall joined to a rear wall along a sealed edge of both of the front wall and the rear wall to form a waste collection cavity between the front wall and the rear wall;

an inlet hole formed in the rear wall and communicating with the waste collection cavity;

a neck portion formed by the front wall and the rear wall, with the neck portion terminating at a discharge opening communicates with the waste collection cavity, the discharge opening formed in the bag between a first unsealed edge of the front wall and a second unsealed edge of the rear wall;

a first plate having a first edge and a parallel second edge, the first edge of the first plate aligned along the first unsealed edge of the front wall;

a second plate having a first edge and a parallel second edge, the first edge of the second plate aligned with the second unsealed edge of the rear wall; and a first fastening strip coupled to a first side of the neck portion, and a second fastening strip coupled to an opposing second side of the neck portion, with the first and second fastening strips adapted to be secured to the first plate and the second plate;

wherein the second edge of the first plate extends between a first tab that is offset away from the first side of the neck portion and a second tab that is offset away from the second side of the neck portion;

wherein the second edge of the second plate extends between a third tab that is offset away from the first side of the neck portion and a fourth tab that is offset away from the second side of the neck portion;

wherein the second edge of the first plate is longer than the first edge of the first plate to locate the first tab and the second tab laterally away from the neck portion of the bag;

wherein the first tab has a curved perimeter edge that curves from the longer second edge of the first plate toward a shorter first edge of the first plate.

10. The bag of claim 1, wherein the first edge of the first plate is longer than a width of the neck portion of the bag and includes a strap member that surrounds the discharge opening.

11. The bag of claim 1, wherein the first tab and the second tab each include a curved perimeter edge that connects with the edge line, and each edge line converges to connect with the shorter first edge of the first plate.

12. The bag of claim 1, wherein the edge line tapers along an acute angle relative to a horizontal line aligned with the first unsealed edge of the front wall, and the first fastening strip is coupled to the neck portion to form the acute angle between the first fastening strip and the neck portion.

13. The bag of claim 9, wherein the first tab connects with the shorter first edge of the first plate by a portion of the curved perimeter edge and by an edge line extending between the shorter first edge of the first plate and the curved perimeter edge.

* * * * *

UNITED STATES PATENT AND TRADEMARK OFFICE
CERTIFICATE OF CORRECTION

Page 1 of 1

PATENT NO.         : 10,813,786 B2
APPLICATION NO.    : 15/326496
DATED              : October 27, 2020
INVENTOR(S)        : Jes Lysgaard It is certified that error appears in the above-identified patent and that said Letters Patent is hereby corrected as shown below:

In the Specification

In Column 1, Line 24, delete "At is" and insert -- At its --, therefor.

In Column 5, Line 22, delete "is lower" and insert -- its lower --, therefor.

In Column 6, Line 6, delete "second edge of the plates 36, 38" and insert -- second edge 36, 38 of the plates --, therefor.

In the Claims

In Column 7, Line 7, in Claim 1, delete "front;" and insert -- front wall; --, therefor.

In Column 7, Line 13, in Claim 1, delete "located a" and insert -- located at a --, therefor.

In Column 7, Line 36, in Claim 5, delete "coversheet" and insert -- cover sheet --, therefor.

In Column 8, Line 5, in Claim 9, delete "communicates" and insert -- that communicates --, therefor.

Signed and Sealed this
Thirteenth Day of July, 2021

Drew Hirshfeld
*Performing the Functions and Duties of the*
*Under Secretary of Commerce for Intellectual Property and*
*Director of the United States Patent and Trademark Office*